United States Patent [19]

Fuqua

[11] Patent Number: 4,601,713
[45] Date of Patent: Jul. 22, 1986

[54] VARIABLE DIAMETER CATHETER

[75] Inventor: Clark R. Fuqua, Salem, Va.

[73] Assignee: Genus Catheter Technologies, Inc., Salem, Va.

[21] Appl. No.: 743,705

[22] Filed: Jun. 11, 1985

[51] Int. Cl.$^4$ ............................................. A61M 25/00
[52] U.S. Cl. ...................... 604/280; 604/96; 604/104; 604/265; 128/343
[58] Field of Search .......... 604/96, 104–109, 604/265–268, 280, 281–282, 95, 170; 128/343, 344

[56] References Cited

U.S. PATENT DOCUMENTS

| | | | |
|---|---|---|---|
| 2,442,573 | 6/1948 | Stafford | 604/104 |
| 3,460,541 | 10/1966 | Doherty . | |
| 3,490,457 | 1/1970 | Petersen . | |
| 3,592,197 | 7/1971 | Cohen | 604/106 |
| 3,736,939 | 6/1973 | Taylor | 604/265 |
| 3,789,852 | 2/1974 | Kim et al. | 604/104 |
| 4,043,346 | 8/1977 | Mobley et al. | 604/107 |
| 4,141,364 | 2/1979 | Schultze . | |
| 4,195,637 | 4/1980 | Gruntzig et al. . | |
| 4,257,422 | 3/1981 | Duncan | 604/282 |
| 4,276,874 | 7/1981 | Wolvek et al. . | |
| 4,309,994 | 1/1982 | Grunwald | 604/284 |
| 4,315,512 | 2/1982 | Fogarty . | |
| 4,401,433 | 8/1983 | Luther . | |
| 4,406,656 | 9/1983 | Hattler et al. . | |
| 4,411,655 | 10/1983 | Schreck | 604/104 |
| 4,451,256 | 5/1984 | Weikl et al. | 128/343 |
| 4,467,790 | 8/1984 | Schiff . | |
| 4,493,711 | 1/1985 | Chin et al. . | |

FOREIGN PATENT DOCUMENTS 1810804 6/1970 Fed. Rep. of Germany .

OTHER PUBLICATIONS

Roy A. Tucker—"History of Sizing of Genitourinary Instruments", *Urology*, Sep. 1982, vol. XX, No. 3, pp. 346–349.

Newman et al., "A General Ureteral Dilated-Sheathing System", *Urology*, vol. XXV, No. 3, Mar. 1985, pp. 287–288.

*Primary Examiner*—C. Fred Rosenbaum
*Assistant Examiner*—Michelle N. Lester
*Attorney, Agent, or Firm*—Stevens, Davis, Miller & Mosher

[57] ABSTRACT

This invention provides a variable diameter catheter which is folded in a longitudinal manner in order to reduce the diameter for convenient and less traumatic insertion into a body orifice.

20 Claims, 15 Drawing Figures

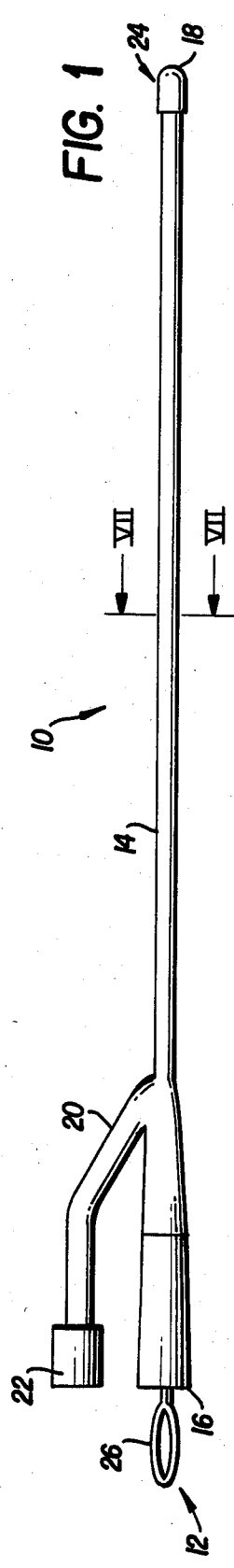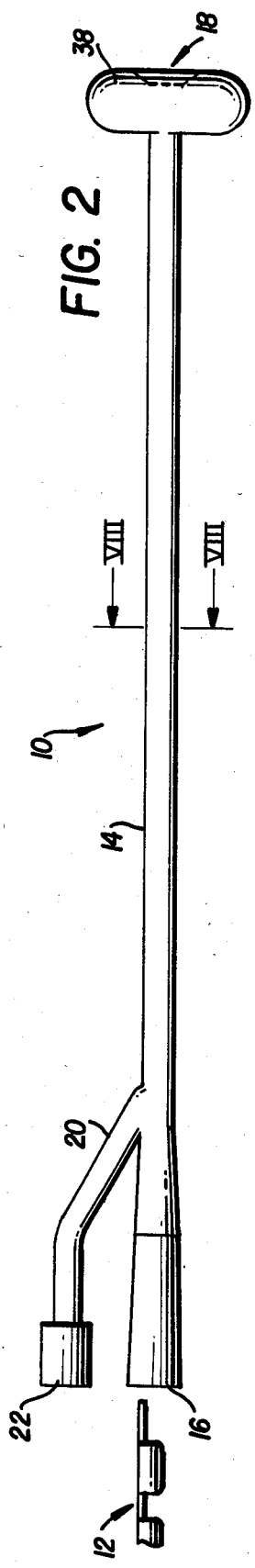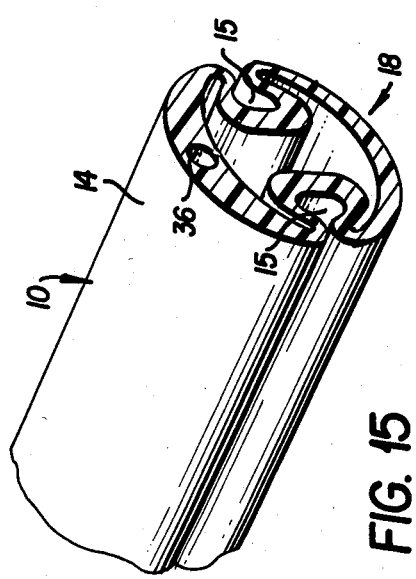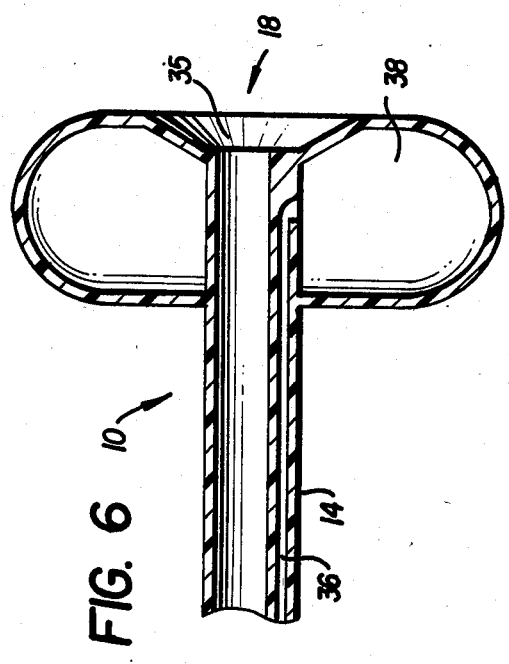

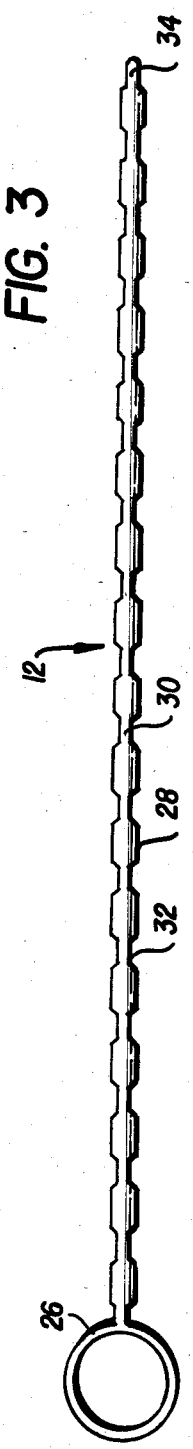
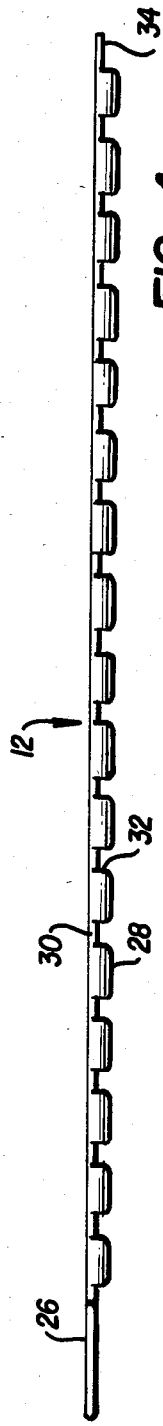
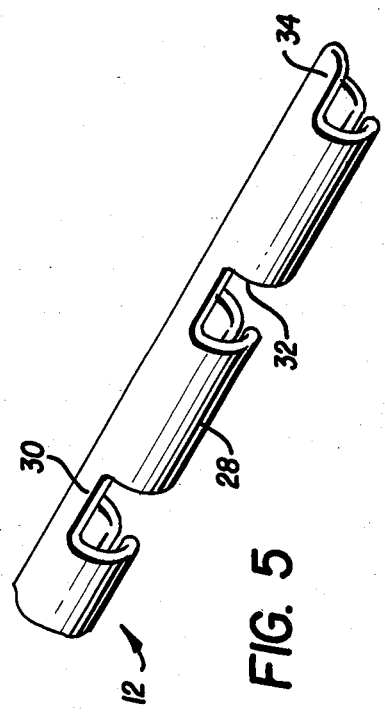

VARIABLE DIAMETER CATHETER

BACKGROUND OF THE INVENTION

1. Field of the Invention

The present invention is directed to medical catheters, and specifically directed to a variable diameter catheter (VDC) in which the diameter of the catheter is decreased for insertion into a body cavity.

2. Description of Prior Art

Catheters are ubiquitous to the medical field, finding importance in a variety of uses. The term "catheter" is commonly used to identify a tubular instrument that is inserted into various body cavities, naturally or surgically opened, and the catheter of the present invention will be understood as intended thus broadly unless the context clearly indicates the contrary. The following list indicates the broad range of uses for catheters:

1. intravenous cannula
2. umbilical catheters
3. endotracheal tubes
4. suction catheters
5. oxygen catheters
6. stomach tubes
7. feeding tubes
8. lavage tubes
9. rectal tubes
10. urological tubes
11. irrigation tubes
12. trocar catheters
13. heart catheters
14. aneurysm shunts
15. stenosis dilators The use of catheters has been recorded from as early as 3000 B.C. An interesting history of eary catheter use may be found in an article by Roy A. Tucker entitled "History of Sizing of Genitourinary Instruments", *Urology*, September 1982, Vol. XX, No. 3, pages 346–349. The earliest catheters were metal tubes generally comprising one or two distinct sizes, depending upon the size of the patient. Catheters such as these were found in the ruins of Pompeii, which were buried in 79 A.D. The development of the modern catheter has been accredited to Lorenz Heister (1683–1758), who made the catheter in the shape of the natural curve of the prostatic urethra. Benjamin Franklin, famous statesman, journalist an scientist, has been accredited with inventing a urethral catheter for use by his brother, a victim of prostatic obstruction.

Perhaps the most significant achievement in the field of catheter design to date is ascribed to the development of the Foley catheter, which was invented around 1945 by Dr. Frederick Foley. This catheter is still very active in the urological market. The Foley catheter is a somewhat rigid latex or plastic tube, which is inserted in the urethral tube optimally by means of a stylet. The stylet is similar in appearance to an opened coat hanger wire. The stylet is placed within the catheter tube, thus allowing some rigidity with the tube is being inserted into the urethral tube. Prior to the development of the Foley catheter, there existed the problem of the patient unconsciously pulling the catheter tube out of the urethra or out of the bladder. The Foley design includes a tube with an inflatable cuff or balloon at the distal end of the catheter so as to hold the catheter in place. The distal end of the catheter shaft is inserted into the patient's urethra during placement, and the shaft is passed through the urethra until the portion of the catheter comprising the balloon is located in the bladder with the proximal end of the catheter located outside the patient's body. The balloon is then inflated in order to retain the catheter in the bladder. During catheterization, urine drains from the bladder through a drainage lumen in the catheter and through a drainage tube connected to the catheter into a drainage bag for collection therein.

Other types of catheters include one developed by Peterson and disclosed in U.S. Pat. No. 3,490,457, which is directed to a catheter inserted into a bladder or other body cavity through a small opening. When the Peterson catheter is in place, a thin, elastic outer sleeve is flexed to fold out a set of radially projecting wings, which prevent the catheter from slipping out of position when in use.

U.S. Pat. Nos. 4,467,790 to Schiff, 4,276,874 to Wolbek et al, and 4,406,656 to Hattler et al are all directed to catheters for intra-aortic use. Schiff is directed to an intra-aortic percutaneous balloon catheter of reduced diameter. A stylet extends through the balloon catheter and is anchored to the catheter tip. The stylet's proximal end is coupled to a control knob assembly which, when twisted, twists the stylet in the tip, causing the balloon to be twisted as it is being lengthened. The lengthening of the balloon prevents the balloon membrane from doubling up as it is twisted. The twisting operation significantly reduces the exterior balloon diameter, enabling the balloon to fit through a small diameter percutaneous sheath inserted into the artery. This causes a blood-type seal, preventing blood from exiting the sheath. Hattler et al are directed to a multi-lumen catheter adapted to be inserted into the vein of a patient through a conventionally-sized insertion needle. The collapsible lumen expands outwardly under the pressure of fluid flow. When fluid flow is absent, the lumen collapses to a smaller cross-sectional area. Wolbek et al are directed to an elongatable balloon intraaortic catheter.

U.S. Pat. Nos. 4,493,711 to Chin et al, 4,195,637 to Gruntzig et al and 4,315,512 to Fogarty are directed to catheters for use in dilating a stenosis or occlusion in a body passageway. Chin et al are directed to a tubular extrusion catheter which provides a means for placement of a soft, non-elastomeric tube through the lumen of a normal or occluded artery, vein or other body passageway. Gruntzig et al are directed to a dilatation catheter in which the outer wall of the catheter is collapsed over an inner support hose. Once installed into the body, the lumen of the catheter is filled with a solution to expand the wall. Fogarty is directed to an elastomeric dilatation balloon catheter which is placed in an occluded section of a blood vessel. The balloon is expanded through the injection of a volume of fluid into the catheter, thereby pressing the occlusion against the wall of the blood vessel, which subsequently removes the occlusion.

The following patents are directed to catheters of varying sizes. U.S. Pat. No. 4,401,433 to Luther is directed to folding a catheter tube in order to reduce its overall size. The catheter is folded by means of arms connected to a catheter folding device as the catheter advances into the device. The folded catheter enters a cannula, which is then inserted into the patient. The preferred shape of the catheter is elliptical and, when properly folded, the catheter is said to have a small cross-sectional area. German Pat. No. 1,810,804 to Metz is directed to the use of a folded catheter in a cannula. Metz employs a "physiological adhesive" to secure the catheter in place. U.S. Pat. Nos. 4,141,364 to Schultze and 4,460,541 to Doherty both disclose balloon-type tubes, wherein the tube is collapsed for insertion and then inflated.

Newman et al, in an article entitled "A General Ureteral Dilated-Sheathing System", *Urology,* Vol. XXV, No. 3, March 1985, pages 287-288, suggest a dilator-sheathing system which consists of four coaxial Teflon (Reg. TM) catheters with external dimensions of 6, 10, 14 and 17 French. The term "French" is well known to the catheter art as an increment of measurement of the diameter of a catheter. To facilitate passage, the larger catheters are tapered on the dilating end so that they approximate the size of the next smaller catheter. In operation, the 6 French (6-F) catheter is advanced to a designated point in the ureter. Then, the 10-F is advanced over the 6-F catheter, and so forth until the 17-F catheter is in place. The three smaller catheters are then removed, leaving the 17-F catheter in place. In this manner, the size of the ureter is gradually increased, which, in theory, reduces trauma to the mucous membranes.

Summarizing the state of the present-day catheters, there are a number of types of catheters in use today. However, it appears that the Foley-type catheter and its variations are predominant in the medical technology market. According to a Frost and Sullivan report, entitled *Prepackaged Kits and Trays-Markets in the U.S.* (#A1139), copyright 1983, "[T]here are more Foley catheter care trays sold than any other single trays or kits. This reflects the common need to catheterize both hospital patients and nursing home residents". However, recent studies in these types of catheters have placed doubt on their effectiveness. Problems, such as infection, inserting the wrong-sized catheter, leakage, and difficulty in insertion, create a plethora of hazards in the catheter industry.

According to Calvin M. Kunin, M.D., in an article entitled "Genital Urinary Infections in the Patient at Risk: Extrinsic Risk Factors", *The American Journal of Medicine,* May 15, 1984, pages 131-139, catheter-induced infections are the most frequent and intractable problem in hospital infection control. Approximately 35% of all nosocomial infections are related to the urinary tract. When used inappropriately, catheters can introduce microorganisms into the bladder and impair host defenses sufficiently to produce infection of the urinary tract. The urethral catheter drains the bladder, but exerts pressure on the mucosa and obstructs the periurethral ducts.

It is also suspected that many of the infections that are caused as a result of an operation come from catheter infections. In most cases, these are not documented, as they are merely passed off as a "post-operative infection".

A study published in a recent issue of the *New England Journal of Medicine* and reported in the Frost and Sullivan report (supra) at page 32, suggests that if the author's sample was expanded nationwide, 56,000 deaths per year might be associated with Foley catheter-related infections. This represents approximately 75 of every 10,000 patients who recently underwent the urological catheterization procedure at short-term general admission hospitals and implies that 14% of all catheterized patients in those hospitals die regardless of cause.

It is believed that one of the major difficulties associated with catheter-induced infections results from the absence of accurate sizing methods being available for insertion through the urethral tube, as sizing generally is the result of "on-site inspection". In other words, the physician or medical technician usually determines what size catheter the patient needs by observing the anatomy of the patient. For example, pediatrics generally require an 8-F to 10-F sized catheter, while a normal adult requires a 16-F to 20-F sized catheter. It is logical to assume that an underestimation results in urine or other body fluid leakage, while overestimation results in trauma to the urethal tissues.

Other difficulties result from the actual insertion of the catheter. Because catheterization has become a fairly standard procedure in medicine today, the insertion process is now generally handled by hospital staff personnel other than physicians. Unless the technician has the requisite skill for inserting a catheter, the insertion process can be rather difficult, resulting in the over-handling of a catheter which can precipitate catheter-induced infections.

While catheterization is documented to be the cause of many infection-related problems associated in the medical industry, it is still considered to be the lesser of two evils. On the one hand, if the physician does not catheterize a patient, the patient may be exposed to uremic poisoning or a burst or tear in the bladder. Because catheters are readily available and very common, a physician will undoubtedly insert a catheter and risk the resulting infection.

OBJECTS OF THE INVENTION

It is an object of the invention to produce a medical catheter which reduces problems relating to infection and patient trauma.

It is also an object of the present invention to produce a catheter which is insertable into a body orifice with a minimum of discomfort and difficulty.

It is further an object of the present invention to produce a catheter in which the diameter of the catheter tube is folded to reduce the overall diameter of the catheter during the insertion process.

Further, it is an object of the present invention to produce a catheter which will aid in the spread of an anti-infective medicant within the body orifice.

It is further an object of the invention to reduce the amount of residual urine in the bladder.

It is further an object of the invention to reduce the size of the catheter tip.

These and other objects will be addressed in the following sections.

SUMMARY OF THE INVENTION

The present invention provides a catheter which may be longitudinally folded for insertion into a first end of a body orifice and then unfolded after insertion for subsequently transporting a fluid, comprising a resiliently flexible tube of generally uniform diameter along its length. The tube comprises walls of uneven thickness around its circumference, such that the wall is longitudinally foldable uon itself, with that portion of the wall which folds upon itself being thinner than the rest of the wall. The catheter further comprises a means for retaining the involution or fold in the catheter tubes, such that the folded tube will unfold to its normal rounded configuration upon removal or release of the retaining means. In this manner, the diameter of the catheter in the folded state is considerably reduced over that of the diameter in the unfolded state.

The present invention is also directed to a catheter which may be longitudinally folded for insertion into a first end of a body orifice and then unfolded after insertion for subsequently transporting a fluid. The catheter comprises a resiliently flexible tube comprising a proximal end and a distal end, the flexible tube being of generally uniform diameter along its length. The flexible tube further comprises a wall of varying thickness around its circumference, such that the wall is longitudinally foldable upon itself, with that portion of the wall which folds upon itself being thinner than the rest of the wall. The diameter of the folded flexible tube is approximately one-half the diameter of the unfolded tube. The flexible tube further comprises a drainage lumen and an inflation lumen, wherein the drainage lumen connects an inflation diaphragm located at the distal ends of the flexible tube to the proximal end of the flexible tube. The inflation lumen is independent of the drainage lumen and adapted to selectively and independently admit an exhaust fluid from the inflation diaphragm. The distal end of the flexible tube is further provided with a single opening extending directly to the drainage lumen. The opening is sealed with a removable sealing means which dissolves upon contact with a liquid. The catheter also includes a stylet, which is interiorly placed within the flexible tube, for retaining the fold in the flexible tube. The stylet is semi-rigid for manipulating the catheter during placement within the body orifice. The stylet comprises a spine and at least one series of ribs emanating from the spine in a circular manner, wherein the ends of each series of ribs approach but do not meet. The rigidity of the stylet is dependent upon the number and length of the ribs.

The present invention is also directed to a method of inserting a variable diameter catheter into a body orifice, which comprises considerably reducing the diameter of the catheter, inserting the folded catheter tube into the body orifice, such that the catheter tube remains in a releasably folded position during the entire insertion process, and unfolding the catheter tube, thus allowing it to regain its unfolded diameter within said body cavity.

The present invention is also directed to a catheter stylet for reducing the diameter of a catheter, in which the stylet comprises at least one series of separated ribs emanating from a spine, in which the ribs emanate from the spine in a circular manner wherein the ends of the ribs approach but do not meet.

BRIEF DESCRIPTION OF THE DRAWINGS

FIG. 1 is a side view of the catheter of the present invention with the stylet in position;

FIG. 2 is a side view of the catheter of the present invention with the stylet retracted;

FIG. 3 is an elevated view of one embodiment of the stylet of the present invention;

FIG. 4 is a side view of the stylet of FIG. 3;

FIG. 5 is a close-up, perspective view of the distal end of the stylet of FIG. 3;

FIG. 6 is a partial sectional view of the distal portion of the catheter of FIG. 2;

FIG. 15 is a perspective view of an alternative embodiment to the catheter of the present invention.

DETAILED DESCRIPTION OF THE INVENTION

Figure 7:
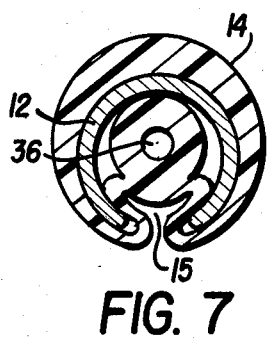
FIG. 7 is an enlarged, cross-sectional view of a preferred embodiment of the folded catheter of FIG. 1, taken along the line VII—VII thereof.
Figure 8:
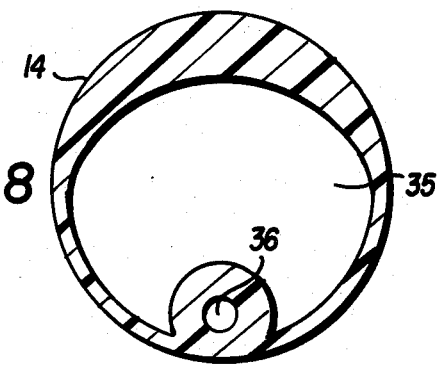
FIG. 8 is an enlarged, cross-sectional view of a preferred embodiment of the fully expanded or rounded catheter of FIG. 2, taken along the line VIII—VIII thereof.

The present invention is directed to the concept that inserting a smaller variable diameter catheter (VDC) into a body orifice will create less trauma to the patient, thereby reducing the risk of infection and the painful effects of catheter placement. The term "body orifice" or "body cavity" is meant to include a natural or surgically prepared body opening. Examples of natural body orifices include the urethral tube, ureter, blood vessels, esophagus and the like. Further benefits of the present invention will be more thoroughly discussed hereinafter. The VDC will now be described with reference to the figures.

FIG. 1 shows VDC 10 with stylet 12 in position. VDC 10 comprises a flexible plastic tube 14 having a proximal end 16 and a distal end 18. Tube 14 is fixedly attached to inflation tube 20, located near proximal end 16 of the VDC. Located at the proximal end of inflation tube 20 is inflation valve 22, which is designed to accept a luer tip syringe (not shown). Distal end 18 is occluded by a removable cap 24, such as a gelatin cap, which will be discussed more thoroughly hereinafter.

Tube 14 may be composed of any standard flexible, nontoxic materials, such as, for example, natural rubber or latex, polypropylene, polyethylene, polyvinyl chloride or silicone. It is desired that the surface of tube 14 be coated with a low-friction material in order to eliminate the tendency to grab the mucous tissues and to prevent a build-up of infection-causing organisms. Materials such as Teflon ® and silicone, as well as others, act to create a low-friction surface.

Advantageously, the VDC of the present invention is folded to reduce the cross-sectional area of the tube by involuting the tube in the longitudinal direction. The VDC is kept in its folded state during the insertion process.

Figure 9:
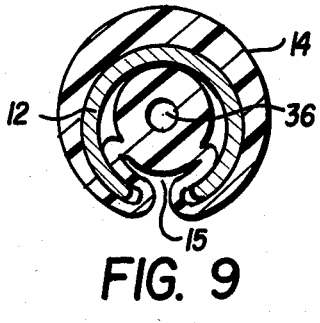
FIGS. 9 and 10 are enlarged, cross-sectional views of a different embodiment of the catheter tube of the present invention in the folded position (FIG. 9) and in the fully expanded position (FIG. 10)
Figure 10:
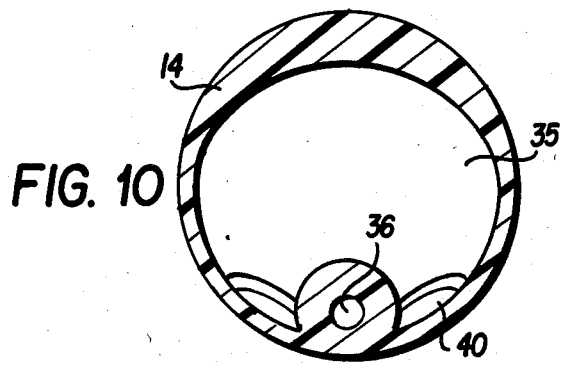
Figure 11:
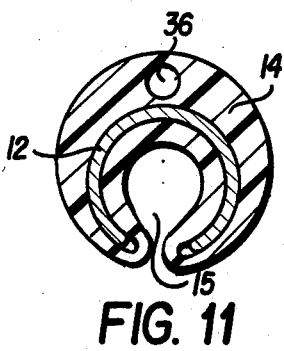
FIGS. 11 and 12 are enlarged, cross-sectional views of a different embodiment of the catheter tube of the present invention in the folded position (FIG. 11) and in the fully expanded position (FIG. 12)
Figure 12:
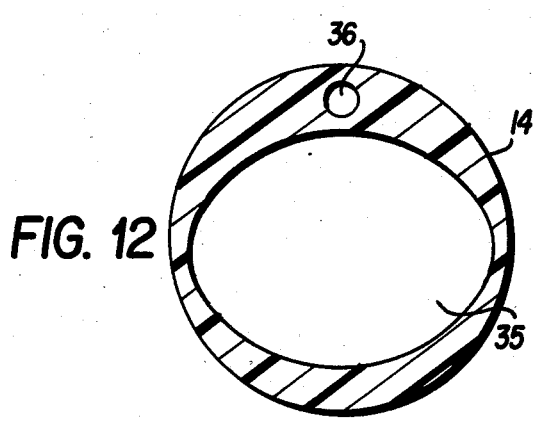

A means for holding the longitudinal fold in place is stylet 12. When stylet 12 is positioned in VDC 10, as shown in FIG. 1, the wall of tube 14 is folded upon itself, thus reducing the external diameter of catheter tube 14 by approximately one-half. Reference is now made to FIGS. 7, 9 and 11, which show a cross-sectional view of varying embodiments of catheter tube 14 with stylet 12 in place, thus creating a fold 15 in catheter tube 14.

Referring now to FIGS. 3–5, stylet 12 comprises pull tab 26 at its proximal end for assisting in the guidance of VDC 10 through a body orifice and for manipulating stylet 12 within catheter tube 14. Stylet 12 may be composed of any relatively rigid material which acts to stiffen the VDC for insertion and which will accommodate sterilization procedures without degradation. Segmented ribs 28, separated by spaces 32, emanate from spine 30 in a circular fashion, as best illustrated in FIG. 5. Stylet 12 is segmented, or separated, to allow the tube to have lateral flexibility. However, if it is desired that the tube have more rigidity, the length of spaces 32 can be reduced. On the other hand, with a larger space 32, the catheter tube 14 becomes more flexible. Thus, stylet 12 can either have large spaces 32 or no spaces at all. For example, it may be desired to insert a completely rigid catheter in which stylet 12 is void of any spaces 32, as in a cardiovascular thoracic-type setting. On the other hand, in a nasal-gastrointestinal tube requiring a great need for bends and curvatures, it may be desired for the tube to be flexible, requiring the need for larger spaces 32.

Distal end 34 of stylet 12 may be either pointed (not illustrated), as in the case of a trocar-type catheter arrangement, or blunted, as disclosed in FIGS. 3–5.

Referring now to a preferred embodiment of the distal end 18 of VDC 10, as illustrated in FIGS. 2 and 6, it can be seen that distal end 18 is at least semi-open-ended. Prior art catheters generally have a plastic-type tip in order to guide the catheter through the body orifice. Eyelets or lumens behind the tip are present to allow fluid flow. An advantage of the open-ended configuration of distal end 18 of the present invention is that a larger opening is available to allow for fluid passage. For urological purposes, it is estimated that the open distal end 18 allows a 200–300% better drainage than with the standard eyelet-type catheters. Because VDC 10 is folded for insertion into the body orifice, the folded shape allows for a more rounded configuration at distal end 18 in order to advance the VDC. Therefore, there is also no need for the plastic-type tip of the prior art.

The tip of distal end 18 must be formed in such a way as to lead the folded catheter into position in the body orifice and to allow the catheter to unfold without hindrance. Different types of catheter tips are contemplated. For example, stylet 12 could be provided with a blunt or pointed tip, depending upon the requirements of the catheter. Another, and a preferred, embodiment is a dissolvable tip, i.e., a gelatin cap, which would disintegrate after a given time upon exposure to body fluids. Such a cap is referred to by numeral 24. Gelatin cap 24 is placed upon distal end 18 of folded catheter 10 to further reduce any incidence of trauma as the catheter is advanced into a body orifice. Because prior art catheters are generally inserted in its full-sized condition, these catheters cannot effectively have an opening at the end of the catheter covered by a gelatin cap. Due to the size of the prior art catheter being inserted into the body orifice, the gelatin cap would readily scrape away as it is being inserted through the urethral tube, leaving an open-ended large diameter catheter advancing into the body orifice.

Because the distal end 18 of VDC 10 is open-ended and has a correspondingly larger accumulated surface area than the prior art eyelet or side lumen openings, salts, minerals, blood clots and other obstructions in the bladder can be more easily removed. Further, the distance from distal end 18 to balloon 38 is generally less than that of the prior art distance between the balloon and the eyelet portion of the catheter. In this manner, the present invention allows for better drainage from the bladder.

FIGS. 7–14 are cross-sectional illustrations of different embodiments of VDC 10 in varying stages of expansion, from the folded position (FIGS. 7, 9, 11 and 13) to the fully expanded or rounded position (FIGS. 8, 10, 12 and 14). A cross-sectional representation of stylet 12 can be seen in each of FIGS. 7, 9 and 11. As can be seen from the cross-sectional views, VDC 10 includes drainage lumen 35 and inflation lumen 36. Inflation lumen 36 runs the length of VDC 10 from inflation valve 22 to an inflation diaphragm or balloon 38. Inflation lumen 36 can be housed within the part of the catheter wall creating the fold 15 of VDC 10, as shown in FIGS. 7–10, or outside fold 15, as shown in FIGS. 11–14, and, in another embodiment, as shown in FIG. 15. Inflation lumen 36 acts as an inflation fluid conduit for inflating balloon 38, as shown in FIGS. 2 and 6. Drainage lumen 35 runs the length of catheter tube 14 from distal end 18 to proximal end 16.

The varying embodiments of the present invention will now be discussed with reference to the figures. FIGS. 7–12 all show cross-sectional views of catheters which will accept stylet 12 as illustrated in FIGS. 3–5. Catheter tube 14, as illustrated in FIGS. 7–12, differ from each other in the position of inflation lumen 36. It can also be seen that the thickness of the walls in FIGS. 7, 8, 11 and 12 differ. This will be explained more fully hereinafter. The embodiment shown in FIGS. 9 and 10 has two bladder walls 40 for receiving fluid. A fluid is inserted into bladder walls 40 in order to give catheter 10 more tensile strength. This would be advantageous if a more rigid and less flexible catheter is desired.

Figure 13:
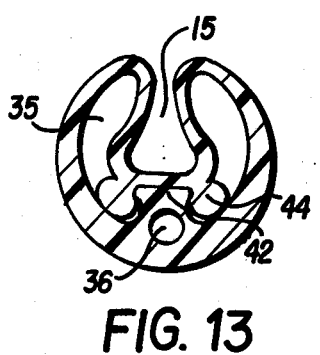
FIGS. 13 and 14 are enlarged, cross-sectional views of a different embodiment of the catheter tube of the present invention in the folded position (FIG. 13) and in the fully expanded position (FIG. 14)
Figure 14:
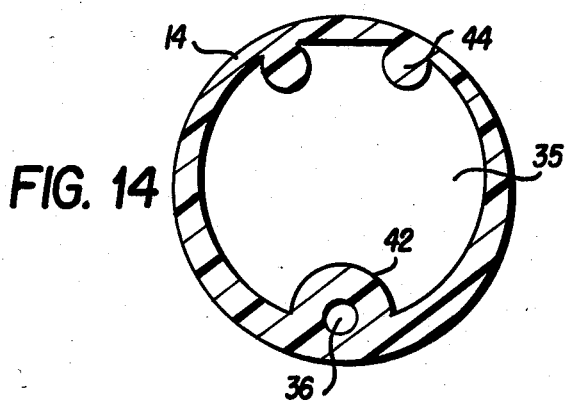

The embodiment shown in FIGS. 13 and 14 is a non-stylus type of catheter, in which the catheter is folded upon itself by means of dorsally placed male rib 42 protruding along the length of the surface of drainage lumen 35, which detachably connects to a double-ribbed female connecting means 44. VDC 10 may then be inserted into a body orifice in the folded configuration without the aid of a stylet. Inflation fluid is then passed through inflation lumen 36. The fluid causes the walls of rib 42 to expand, thus releasing the connection between rib 42 and female connecting means 44 and unfolding the catheter. The advantages to this embodiment are that it does not require a stylet, and thus a stylet does not have to be removed after the catheter has been inserted.

A further embodiment is shown in FIG. 15. This embodiment has a double fold 15 and would require the surfaces of a double-edge stylet (not shown). The double-edge stylet is similar to the stylet of FIGS. of 3–5, with the exception that it would comprise an additional set of ribs 28 extending from spine 30 in a mirror-image fashion. The advantages of the catheter of this embodiment are that it has a stronger tensile strength and the catheter tube can be better adjusted for traversing strictures and curves. Although the embodiment of FIG. 15 is less flexible in a lateral movement, it has more up-and-down flexibility. This embodiment would probably best be used as a feeding tube. Advantageously, the tube can be inserted half its normal size and then, when it opens, will allow a greater amount of feeding fluid to enter the body, due to the larger lumen size and the absence of the flow-restricting eyelets at the distal end of the catheter.

The advantages of the catheter of the present invention over the prior art lies in the shape and conformity of the walls of the catheter tube 14 and in the physics of the wall structure. Prior to the present invention, it was not known to alter the thickness of the wall to accommodate the folding of the catheter tube. By conforming that part of the catheter wall which will accept the tension of the fold to be thinner compared to the rest of the catheter wall, the catheter can be advantageously folded to a size approximately one-half of its original unfolded size without the problems of stress or crack in the walls due to the folds. Thus, in the embodiments shown in FIGS. 7–10, the walls at the ventral position are thinnest relative to the remaining wall structure of the tube. The walls at the dorsal position of the tube are thickest relative to the remaining wall structure, and the walls at the laterally opposed positions are increasingly thickened from the ventral to the dorsal position. Therefore, this uneven thickness of the walls allows the catheter wall structure to be folded upon itself with the aid of the stylet, such that the diameter of the folded catheter tube 14 is approximately one-half the diameter of the unfolded tube.

It is to be noted that the shape and thickness of the tube itself can be modified, depending upon need. For example, the rigidity can be increased or decreased, depending on whether the tube is to be snapped open quickly or gently unfolded. Thus, if the VDC is designed to assist in the evacuation of a chest cavity, it must be opened immediately. The catheter wall thickness may be increased so that more of a snap-opening is obtained. In drainage tubes for use in healing wounds, there is a need to have the tube just barely opened until the wound heals and then have the tube shut down. The thickness of this tube may be modified accordingly. Unfolding the catheter of the present invention can be controlled by the speed with which the stylet is pulled from the tube. In this manner, the faster the stylet is pulled from the tube, the faster the whole catheter will expand.

In use, the VDC is removed from suitable packaging (not shown). While the VDC is in the folded state, an operator inserts same into a body orifice. If the VDC requires a stylet, the stylet is then removed, allowing the VDC to expand in conformity with the body orifice.

The advantages of the catheter of the present invention are several. First, the insertion process of the catheter is much easier. A catheter which is almost pediatric in size, i.e., 9-F, can be inserted into an adult. The insertion of a smaller tube is less traumatic and painful, and will cause much less scoring, stretching and scarring during the insertion process. It should also reduce the infection rate.

Another advantage of the tube of the present invention is that the bladder will be drained at a lower level than is normally accomplished with prior art catheters. Usually, the drainage level is only at the level of the eyelet. However, the opening of the catheter of the present invention is lower than that in the catheters of the prior art, thus allowing for bladder drainage. This is important in infection control, because urine generally comprises a great deal of minerals, salts, etc., which could cause a clot to develop, blocking the eyelets. Additionally, because the catheter of the present invention has a larger surface area and it is lower in the bladder, it is believed that there will be much less mineral stoppage in the catheter.

Further, by inserting a catheter one-half the approximate unfolded size into a body orifice, and then adjusting the diameter of the tube, the diameter of the catheter tube can be brought up to the diameter of the body orifice, which is far less painful and much less damaging to the interior surface of the body orifice, as compared to inserting the catheter tube at its maximum diameter.

Another advantage of the catheter of the present invention over those of the prior art is directed to the application of an anti-infective medication into the body orifice as the catheter is being placed therein, in order to reduce the chances of infection. It is well known that one way of combating infection is to coat a catheter tube with an anti-infection type of medication. However, with full diameter or Foley-type catheters, the catheter tubes fit tightly into the body orifice, causing the anti-infection medication to rub off at the entrance of the body orifice. Therefore, it can be expected that the entrance or proximal end of the body orifice has a build-up of anti-infection medication, while the distal end of the body orifice will receive virtually no medication. With the catheter of the present invention, the anti-infection medication may be placed in fold 15 of catheter tube 14. Because the catheter tube is folded during the insertion process, fold 15 shields the anti-infection medication so that it is not removed during the insertion process. Once the tube is inserted into the bladder, the catheter is allowed to resume its normal shape. The anti-infection medicine is thus pushed out of fold 15 and spread around the catheter tube. Therefore, the anti-infection medication will completely surround all of catheter tube 14. Examples of anti-infection medication include heparin and iodine.

The VDC is also economically advantageous. Presently, medical centers must stock catheters having a variety of diameters, e.g., 6-F, 8-F, 10-F, 12-F, 14-F, 16-F, 18-F, 20-F, etc. Because the VDC readily adapts to the restrictions of the opening of the body orifice, it is not necessary to stock the previously required sizes. For example, a 10-F unfolded VDC will accommodate body orifices sized from 8-F to 12-F. Thus, it is possible to accommodate a larger range of catheter size with fewer VDC's.

The VDC of the present invention is well adapted to be used for virtually any purpose known for catheter technology. This includes use as a urological catheter, feeding tube, percutaneous catheter, kidney tubes, cardiovascular catheters, and catheters for removing strictures or occlusions in veins or other body orifices. Non-limiting examples of utilizing a VDC follows.

For urological purposes, there are two prevalent techniques for inserting a catheter into the urinary bladder. One technique is to insert the catheter through the urethra, as has been previously described. Another technique is to insert the catheter directly through the suprapubic area. Suprapubic insertion may be made with an incisional insertion or a punch technique using a trocar. Such an insertion is made either by major surgery, requiring the use of a regional or general anesthesia, or by means of a large hollow trocar puncturing device. A trocar used in this manner is smaller in diameter than the catheter and acts as a rigid guide for the catheter insertion process. Because of the catheter size, the opening left by the catheter is the same diameter as the catheter itself. Over a period of time the diameter of the opening in the bladder may increase causing urine leakage around the opening. The advantage of the VDC is in the insertion of the catheter of a smaller diameter. As the VDC expands it will create a positive pressure against the bladder opening thereby avoiding urine leakage.

Kidney tubes are used to evacuate kidney stones. The tubes are generally passed through the urethra into and past the bladder into the kidney. Problems occur, in that once past the bladder, it is difficult to get a tube that is small enough to pass through the porous areas of the kidneys to evacuate the stones. However, the smaller diameter catheter of the present invention would be superior for insertion into the kidney area. After insertion, the tube would be allowed to unfold to full size in order to evacuate the stone.

Another use for the catheter of the present invention would be in removing strictures or occlusions in veins or other body orifices. In the prior art, a stricture or occlusion was removed by means of a balloon attached to a catheter tube. The deflated balloon portion of the catheter would be inserted into the body orifice to the point of occlusion. The balloon would then be inflated in order to remove the stricture. However, the VDC utilizes a folded catheter tube which is inserted into the stricture portion. The stylet would then be removed in such a manner that only the portion of the catheter tube adjacent the stricture would be allowed to unfold, thus eliminating the stricture. The stylet would then be reinserted into the full length of the catheter and the catheter would be removed. Advantages to this procedure include the absence of the necessity for a balloon and the use of a catheter which has a diameter approximately one-half normal size.

Although the present invention has been described with preferred embodiments, it is to be understood that modifications and variations may be resorted to, without departing from the spirit and scope of this invention, as those skilled in the art will readily understand.

I claim:

1. A catheter adapted to be longitudinally folded for insertion into a first end of a body orifice and then unfolded after insertion for subsequently transporting a fluid, comprising:

a resiliently flexible tube of generally uniform diameter along its length, said tube having a wall of varying thickness around its circumference, such that said wall is longitudinally foldable upon itself, with that portion of said wall which folds upon itself being thinner than the rest of the wall; and means for retaining a fold in said tube, said catheter tube having sufficient resilient memory, such that said folded tube will unfold to its normal rounded configuration upon removal or release of said retaining means.

2. The catheter according to claim 1, wherein said tube includes a drainage lumen and an inflation lumen.

3. The catheter according to claim 2, wherein said flexible tube includes a proximal end a distal end, and an inflatable diaphragm disposed adjacent said distal end, said inflation lumen connecting said diaphragm to an opening in said proximal end of said tube, said inflation lumen being independent of said drainage lumen and being adapted to selectively and independently admit and exhaust fluid from the diaphragm.

4. The catheter according to claim 3, wherein said distal end is provided with a single opening communicating with said drainage lumen.

5. The catheter according to claim 4, wherein said opening is sealed with a removable sealing means.

6. The catheter according to claim 5, wherein said sealing means is adapted to dissolve upon contact with a liquid.

7. The catheter of claim 6, wherein said sealing means is a gelatin capsule.

8. The catheter according to claim 3, wherein said distal end is recessed from the outer walls of said diaphragm when said diaphragm is inflated.

9. The catheter according to claim 1, wherein said retaining means is placed within said flexible tube.

10. The catheter according to claim 9, wherein said retaining means comprises a semi-rigid stylet for manipulating said catheter during placement within said body orifice.

11. The catheter according to claim 10, wherein said stylet comprises at least one series of pairs of rib elements emanating from a spine member the rib elements of each said pair emanating from said spine member in a circular manner so that their ends approach but do not meet.

12. The catheter according to claim 10, wherein the rigidity of said stylet is dependent upon the number of pairs of rib elements in said at least one series and the width of said rib elements.

13. The catheter according to claim 1, wherein the diameter of said folded flexible tube is approximately one-half the diameter of said unfolded flexible tube.

14. The catheter according to claim 3, wherein said drainage lumen comprises a plurality of collapsible lumens, each having a fluid passageway formed therein.

15. The catheter according to claim 2, wherein said retaining means comprise a male connecting member and a female connecting member formed on the wall of said drainage lumen and adapted to interconnect so as to fold the wall of said tube upon itself and to retain said fold.

16. The catheter according to claim 1, wherein the composition of said catheter tube is selected from the class of materials consisting of polyethane, rubber, elastomers and polyvinylchloride.

17. The catheter according to claim 1, wherein anti-infection medication is placed within the fold of said flexible tube.

18. A catheter and stylet assembly, the catheter being adapted to be longitudinally folded for insertion into a first end of a body orifice and then unfolded after insertion for subsequently transporting a fluid, the catheter comprising:

a resiliently flexible tube including a proximal end and a distal end, said flexible tube being of generally uniform diameter along its length, said flexible tube having a wall of varying thickness around its circumference, such that said wall is longitudinally foldable upon itself, with that portion of said wall which folds upon itself being thinner than the rest of said wall, wherein the diameter of said folded flexible tube is substantially smaller than the diameter of said unfolded tube, said flexible tube further including a drainage lumen, an inflation lumen, and an inflatable diaphragm disposed adjacent said distal end, said inflation lumen connecting said inflatable diaphragm to said proximal end of said flexible tube, said inflation lumen being independent of said drainage lumen and adapted to selectively and independently admit and exhaust fluid from said inflatable diaphragm, said distal end of said flexible tube being further provided with a single opening communicating with said drainage lumen, said opening being sealed with a removable sealing means which is adapted to dissolve upon contact with a liquid; and the stylet being adapted to be placed within said flexible tube for retaining fold in said flexible tube, said stylet being semi-rigid for manipulating said catheter during placement within said body orifice, said stylet comprising: a spine member and at least one series of pairs of rib elements emanating from said spine member, the rib elements of each said pair emanating from said spine member in a circular manner so that their ends approach but do not meet, the rigidity of said stylet being dependent upon the number of pairs of rib elements in said at least one series and the width of said rib elements.

19. A method for inserting a catheter tube into a body orifice, comprising:
(a) folding said catheter tube along its longitudinal length, wherein said tube provides a memory of a normal distended configuration, said folding being conducted and held by a retaining means;
(b) inserting said folded catheter tube into said body orifice; and
(c) removing said retaining means, thus causing said catheter tube to unfold.

20. A method for removing an occlusion in a body orifice, comprising:
(a) folding a catheter tube along its longitudinal length, wherein said tube provides a memory of a normal distended configuration, said folding being conducted and held by a retaining means;
(b) inserting said folded catheter tube into said body orifice through the area of occlusion; and
(c) removing said retaining means from the portion of said catheter tube adjacent said occlusion, such that said catheter tube adjacent said occlusion will unfold in response to said memory.

* * * * *